United States Patent
Ren

[11] Patent Number: 6,159,219
[45] Date of Patent: *Dec. 12, 2000

[54] STENT RETRIEVAL DEVICE

[75] Inventor: Brooke Qin Ren, Champlin, Minn.

[73] Assignee: Scimed Life Systems, Inc, Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/857,791

[22] Filed: May 16, 1997

[51] Int. Cl.[7] .................................... A61F 11/00
[52] U.S. Cl. .................. 606/108; 623/1; 623/11; 623/12; 606/192; 606/198; 604/96.01; 604/103.06; 604/103.07
[58] Field of Search .................. 606/191.2, 108; 604/96–104, 96.01, 103.06, 103.07; 623/1, 11, 12

[56] References Cited

U.S. PATENT DOCUMENTS

| | | |
|---|---|---|
| 5,197,978 | 3/1993 | Hess ........................ 606/194 |
| 5,316,016 | 5/1994 | Adams et al. . |
| 5,352,199 | 10/1994 | Tower ...................... 606/194 |
| 5,690,670 | 11/1997 | Davidson ................. 606/192 |
| 5,695,498 | 12/1997 | Tower ...................... 606/108 |

OTHER PUBLICATIONS

Three Abstracts: British Cardiac Society Abstract Reproduction Form, date unknown.

Abstract: Scientific Sessions Abstract Form, Am. Heart Association, No. 001692, date May 5, 1995.

*Primary Examiner*—Glenn K. Dawson
*Attorney, Agent, or Firm*—Vidas, Arrett & Steinkraus, P.A.

[57] ABSTRACT

The present invention provides a device and method for retrieving a balloon expandable stent which has been misplaced. It utilizes a balloon catheter which is sized to fit into the inside diameter of a stent to be retrieved. The stent has proximal and distal ends and a predefined expansion force threshold which must be exceeded in order to radially expand the stent. The balloon has proximal and distal ends, a greater axial length than the stent to be retrieved, and is made of a compliant material which will deform at less than the predefined expansion force threshold of the stent.

6 Claims, 1 Drawing Sheet

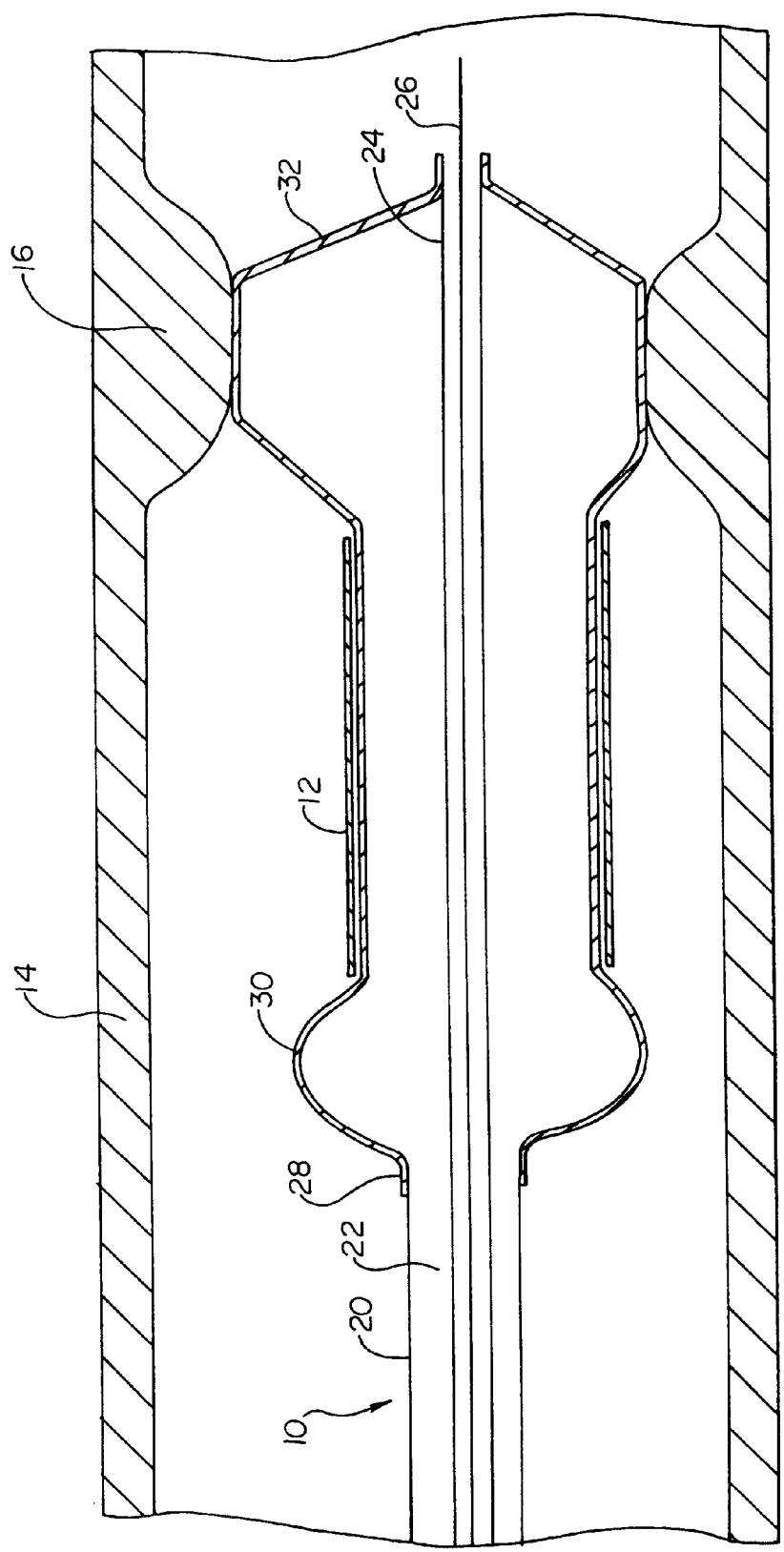

STENT RETRIEVAL DEVICE

BACKGROUND OF THE INVENTION

The present invention relates generally to a stent retrieval device, and more specifically to a stent retrieval device for retrieving a misplaced stent.

Stents are used in a wide variety of medical procedures such as percutaneous transluminal angioplasty (PTA), percutaneous transluminal coronary angioplasty (PTCA), and many other well known procedures. There are several types of stents, including balloon expandable stents and self-expanding stents. Examples of balloon expandable stents are disclosed in U.S. Pat. No. 4,733,665 to Palmaz, U.S. Pat. No. 5,449,373 to Pinchasik et al and PCT WO 96/03092 to Israel. An example of a self-expanding stent is disclosed in U.S. Pat. No. 5,037,427 to Harada. These stents can be delivered using a wide variety of medical devices, including over the wire (OTW) catheters, single operator exchange (SOE) catheters and fixed wire catheters.

Balloon expandable stents are typically carried on a non-compliant balloon, which is inflated at high pressure to expand the inside diameter of the stent, forcing it against the vessel interior walls. A typical balloon expandable stent requires a pressure greater than 2 atmospheres to overcome the expansion force threshold of the stent. Balloons are classified as compliant, semi-compliant and non-compliant. For purposes of this application a non-compliant balloon will radially expand 2–7% greater than its nominal diameter at 6–12 atmospheres; a semi-complaint balloon will radially expand 7–16% greater than its nominal diameter at 6–12 atmospheres and a compliant balloon will radially expand 16–40% greater than its nominal diameter at 6–12 atmospheres. See U.S. Pat. No. 5,556,383 to Wang et al for a discussion of balloon compliance. Also for purposes of this application a non-compliant balloon has a flexural modulus of greater than 250,000 psi; a semi-compliant balloon has a flexural modulus of between 180,000 and 250,000 psi and a compliant balloon has a flexural modulus of less than 180,000 psi.

During a medical procedure a stent can become misplaced, either due to improper location, failure to expand properly, partially dislodge from the balloon or completely dislodge from the balloon. One common problem is caused by the stent contacting a guide catheter and becoming completely dislodged from the balloon. In such as case, a self-expanding stent which fails to expand fully or a balloon expandable stent which has not been expanded is loose in the vasculature.

Often for lack of any other alternative the physician attempts to utilize a typical balloon catheter to retrieve the stent. In this case typical means a non-compliant balloon which must be operated at high pressure. Since most stents can be expanded by exceeding their expansion force threshold with a pressure greater than 2 atmospheres, using a typical balloon can be problematic and the retrieval is often unsuccessful.

What is needed is a stent retrieval catheter with a specialized balloon which allows for retrieval of a stent which has been misplaced without the danger of expanding the stent during the retrieval operation.

SUMMARY OF THE INVENTION

The present invention provides a device and method for retrieving a balloon expandable or self-expanding stent which has been misplaced. It can be used to retrieve any type of stent misplaced in any type of medical procedure. It utilizes a balloon catheter which is sized to fit into the inside diameter of the stent to be retrieved. The stent has proximal and distal ends and a predefined expansion force threshold which must be exceeded in order to radially expand the stent. The balloon has proximal and distal ends, a greater axial length than the stent to be retrieved, and is made of an extremely compliant material which will deform or yield at less than the predefined expansion force threshold of the stent.

The distal end of the stent retrieval device is positioned inside the stent to be retrieved. The balloon is expanded into contact with the stent and the proximal and distal ends of the balloon deform or yield with a pressure less than the expansion force threshold of the stent, which is typically less than 2 atmospheres. Most preferably the balloon will deform or yield at about 1 atmosphere. Upon inflation the balloon forms a dogbone or dumbbell shape with the stent carried for retrieval between the proximal and distal dumbbell deformed balloon ends. The stent retrieval catheter may then be withdrawn from the body or withdrawn into a guide catheter for removal from the patient.

In the preferred embodiment a balloon made of a blend of between 50–5% PBT (polybutylene terephthalate) and 50–95% PETG (glycol-modified polyethylene terephthalate) is preferred. Therefore the preferred ratio of PBT to PETG ranges from 1:1 to 1:19, by weight. U.S. Pat. No. 5,316,016 to Adams discloses a balloon made from a blend of PBT and PETG, but its ratio of PBT to PETG ranges from 9:1 to 1:1, or PBT 90–50% and PETG 10–50%, by weight. The entire contents of U.S. Pat. No. 5,316,016 are hereby incorporated by reference.

The most preferred blend of the inventive stent retrieval balloon material is 25% PBT and 75% PETG, or a ratio of 1:3 by weight. This material provides the desired deformation or yield at approximately 1 atmosphere, which is less than the stent expansion force threshold. Another preferred property of this balloon material is that the proximal and distal ends of the balloon deform simultaneously. This is desirable because if the proximal end of the balloon yields or deforms first, such as with a silicone or latex balloon, the stent may be urged distally.

Extremely compliant silicone or latex balloons can be utilized, but require pretreatment in order to obtain the simultaneous proximal and distal deformation desired. Pretreatment can consist of prestretching the distal balloon end or making the distal end thinner.

BRIEF DESCRIPTION OF THE FIGURE

FIG. 1 shows a misplaced stent being retrieved by the inventive stent retrieval catheter, with the balloon positioned inside the stent to be retrieved and expanded into frictional engagement with the stent and with the proximal and distal ends of the balloon deformed into a dogbone or dumbbell shape.

DESCRIPTION OF THE PREFERRED EMBODIMENTS

Referring to FIG. 1, the inventive stent retrieval device is shown generally at 10 retrieving misplaced stent 12 in lumen 14 near lesion 16. The stent retrieval device includes a catheter 20, balloon inflation lumen 22, guide wire lumen 24 and guide wire 26. As is well known in the art, the balloon 28 is attached to catheter 20 and guide wire lumen 24 for inflation via inflation lumen 22.

In operation, the stent retrieval device is advanced until the distal balloon end has been positioned inside the stent to be retrieved. Balloon 28 is then expanded at a pressure which is less than the expansion force threshold of the stent to be retrieved, which is typically less than 2 atmospheres. Because the balloon 28 is manufactured of an extremely compliant material, it will deform at less than the 2 atmospheres to form the dogbone or dumbbell shape shown in FIG. 1. The stent 12 is frictionally engaged with balloon 28 and carried for retrieval between the dogbone or dumbbell shaped deformed proximal and distal ends 30 and 32 of the balloon. Once the stent 12 has been captured, the stent retrieval device and stent are withdrawn from the body or into a guide catheter (not shown) for removal from the body of the patient.

The balloon is preferably constructed of semi-crystalline or amorphous blend materials, and more preferably of a blend of PBT and PETG, with a ratio of PBT to PETG ranging from 1:1 to 1:19, by weight. In the preferred embodiment the ratio is 1:3 or 25% PBT and 75% PETG, by weight. The preferred balloon material will deform or yield at approximately 1 atmosphere and both the proximal and distal balloon ends 30 and 32 will deform simultaneously. Simultaneous deformation of balloon ends 30 and 32 is desired to ensure that the stent is not urged distally, as would be the case if the proximal end 30 deformed first. It has been found in testing that the preferred material will deform or yield 300–400% at 1 atmosphere. By comparison, the PBT/PETG blend disclosed in Adams U.S. Pat. No. 5,316,016 will not deform until 3–4 atmospheres, which is greater than the typical stent expansion force threshold of 2 atmospheres.

To make the balloon of the preferred embodiment the balloon must be blown at a pressure of between 60–80 psi at between 80–85° C. Conventional balloons are typically blown at a pressure of between 300–500 psi. In order to prevent crystallization the balloon of the preferred embodiment must be sterilized using gamma radiation, rather than the conventional ethylene oxide method.

The typical stent is approximately 20 mm long and it has been found that balloon 28 should preferably be at least twice the axial length of the stent to be retrieved, and most preferably 3–4 times as long as the stent to be retrieved.

Silicone or latex balloons, such as those sold by Specialty Manufacturing, a division of Dow Chemical, can also be utilized, as long as they deform at less than 2 atmospheres of pressure. However, these materials require an additional pretreatment step in order to ensure the desired simultaneous deformation of the proximal and distal ends of the balloon. This pretreatment step can either be prestretching the distal end of the balloon or making the distal end thinner.

Although preferred, it is not critical that both ends of the balloon deform simultaneously. It is important that the distal end deform with or before the proximal end in order to prevent the stent from being pushed or urged distally.

It can be seen from the preceding disclosure that the inventive stent retrieval device can be used to retrieve any type of misplaced stent from any location in the body, as long as the stent retrieval device can be positioned inside the stent to allow capture by inflation of the inventive fixed wire, single operator exchange or over the wire balloon. It can be used with a guide catheter or by itself.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent retrieval device in combination with a stent the combination comprising:

a stent to be retrieved from a body lumen, the stent having proximal and distal ends, a predetermined inside diameter and predetermined axial length;

a balloon catheter sized to fit into the inside diameter of the stent to be retrieved;

the balloon having proximal and distal ends, a greater axial length than the stent to be retrieved, wherein the balloon is constructed of a blend of polybutylene terephthalate (PBT) and glycol-modified polyethylene terephthalate (PETG) having a ratio of PBT to PETG of 1:3 by weight, whereby the stent is captured when the balloon is expanded inside the stent such that the proximal and distal ends of the balloon will deform to a diameter greater than the diameter of the stent, the stent will be frictionally engaged with the balloon without expanding the stent and where the stent is carried for retrieval between the proximal and distal deformed ends of the balloon.

2. A stent retrieval device in combination with a stent the combination comprising:

a stent to be retrieved from a body lumen, the stent having proximal and distal ends, a predetermined inside diameter, a predetermined axial length and a predefined expansion force threshold;

a balloon catheter sized to fit into the inside diameter of the stent to be retrieved;

the balloon having proximal and distal ends, a greater axial length than the stent to be retrieved, and being made of a compliant material which will deform at less than the predefined expansion force threshold of the stent, wherein the balloon is constructed of a material which has been pretreated such that the distal end of the balloon will deform simultaneously with the proximal end, whereby the stent is captured when the balloon is expanded inside the stent such that the proximal and distal ends of the balloon will deform to a diameter greater than the diameter of the stent, the stent will be frictionally engaged with the balloon without expanding the stent and where the stent is carried for retrieval between the proximal and distal deformed ends of the balloon.

3. The stent retrieval device of claim 2 wherein the balloon has been pretreated by prestretching the distal end of the balloon.

4. The stent retrieval device of claim 2 wherein the balloon has been pretreated by making the distal end of the balloon thinner than the proximal end of the balloon.

5. The stent retrieval device of claim 2 wherein the balloon is constructed of a silicone or latex material.

6. A stent retrieval device in combination with a stent the combination comprising:

a stent to be retrieved from a body lumen, the stent having proximal and distal ends, a predetermined inside diameter, a predetermined axial length and a predefined expansion force threshold;

a balloon catheter wherein the balloon is constructed of an extremely compliant material which will deform at less than the predefined expansion force threshold of the stent to be retrieved, the balloon material being constructed of a blend of polybutylene terephthalate (PBT) and glycol-modified polyethylene terephthalate (PETG) having a ratio of PBT to PETG of 1:3 by weight.

* * * * *